United States Patent [19]

Wertz et al.

[11] Patent Number: 4,777,021

[45] Date of Patent: Oct. 11, 1988

[54] MANIFOLD VACUUM DEVICE FOR BIOCHEMICAL AND IMMUNOLOGICAL USES

[75] Inventors: Richard K. Wertz, 1050 46th St., Sacramento, Calif. 95819; Linda R. Watkins, Sacramento, Calif.

[73] Assignee: Richard K. Wertz, Sacramento, Calif.

[21] Appl. No.: 27,827

[22] Filed: Mar. 19, 1987

Related U.S. Application Data

[63] Continuation-in-part of Ser. No. 856,647, Apr. 25, 1986, abandoned.

[51] Int. Cl.⁴ .............................................. B01L 11/00
[52] U.S. Cl. .................................. 422/101; 435/301; 436/178
[58] Field of Search ............... 435/284, 285, 293, 300, 435/301, 311, 299; 422/101, 100; 436/177, 809, 178; 210/406, 323.1, 500.28

[56] References Cited

U.S. PATENT DOCUMENTS

| | | | |
|---|---|---|---|
| 4,246,339 | 1/1981 | Cole et al. | 422/101 |
| 4,407,943 | 10/1983 | Cole et al. | 436/809 |
| 4,427,415 | 1/1984 | Cleveland | 422/101 |
| 4,493,815 | 1/1985 | Fernwood et al. | 436/177 |
| 4,526,690 | 7/1985 | Kiovsky et al. | 422/101 |
| 4,642,220 | 2/1987 | Bjorkman | 435/300 |
| 4,645,602 | 2/1987 | Barnes, Jr. et al. | 210/490 |
| 4,704,255 | 11/1987 | Jolley | 436/177 |

Primary Examiner—Samuel Scott
Assistant Examiner—Noah Kamen
Attorney, Agent, or Firm—Owen, Wickersham & Erickson

[57] ABSTRACT

A device for simultaneously performing multiple biochemical or immunological reactions. A manifold plate rests atop a waste fluid collection chamber or receptacle suitable for attachment to a vacuum pump. The manifold contains a series of wells that serve as reaction vessels. The sides of each well are fluid-impermeable, and its lower end provides a planar, annular base. A hydrophobic membrane is sealed to the lower surface of the base of each well. The membrane is formed of a material through which fluid can be drawn upon application of vacuum while retaining the fluid within the well in the absence of vacuum. By placement of a solid-phase support for binding biological coreactants atop the membrane prior to initiation of the reaction, solid-phase reaction products can be collected when vacuum is applied and can then be freely withdrawn from its well. The membranes of all of the reaction wells are physically isolated from each other so that totally independent biochemical or immunological reactions can be performed in each well without danger of cross-contamination between wells.

12 Claims, 3 Drawing Sheets

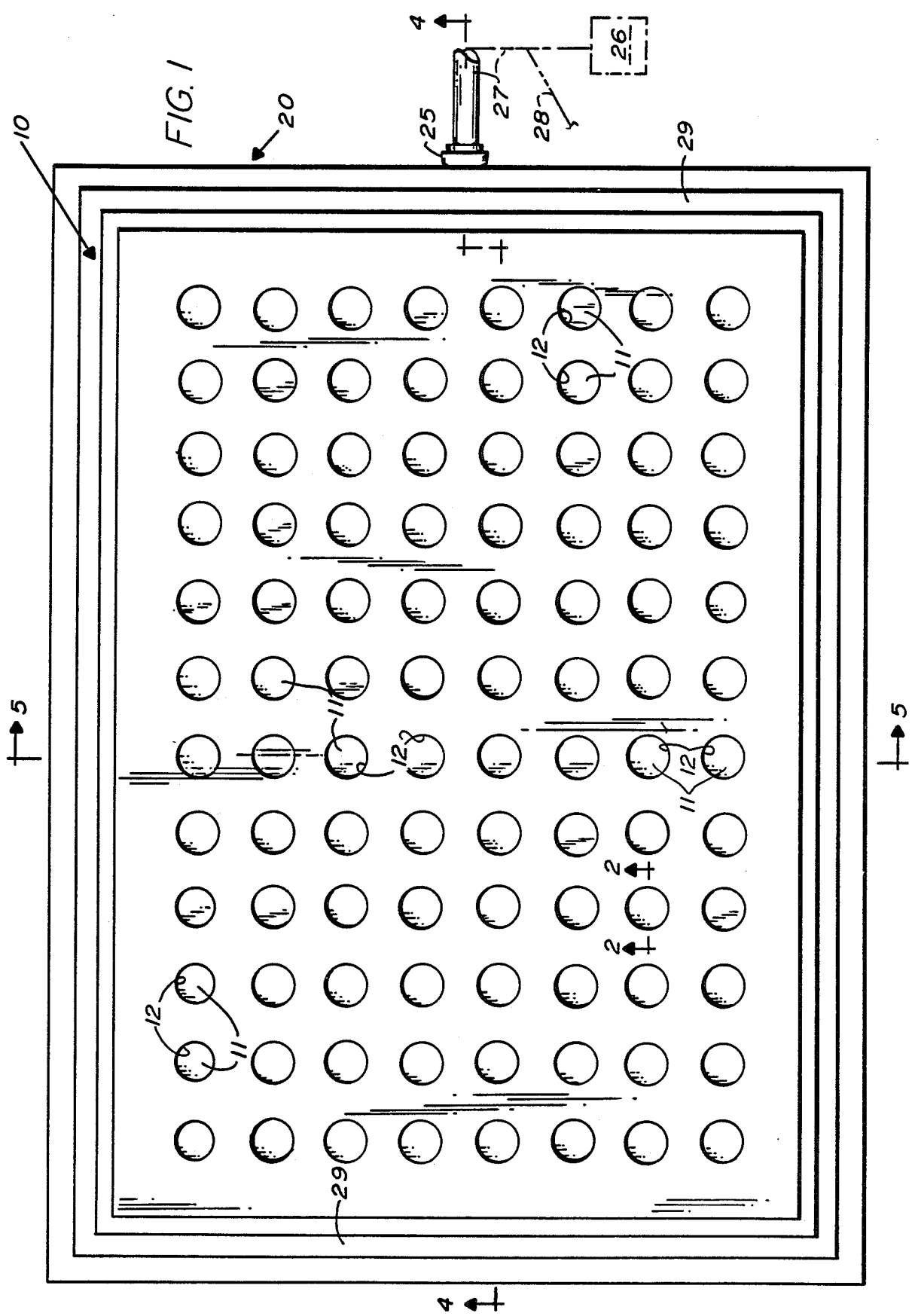

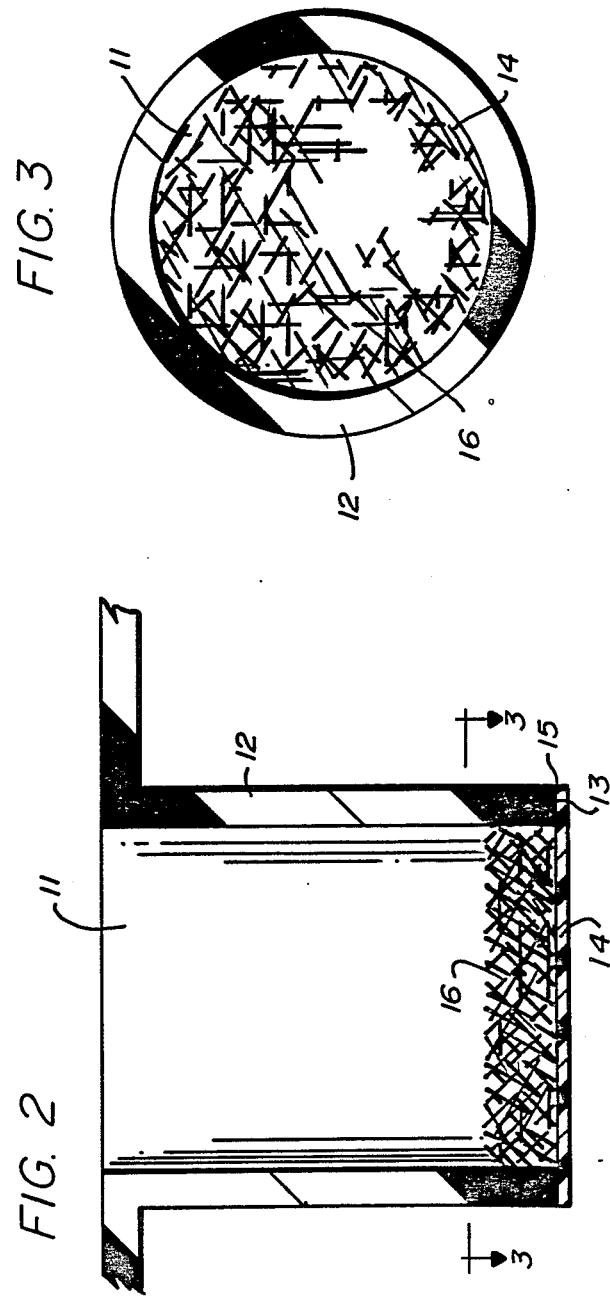
FIG. 3
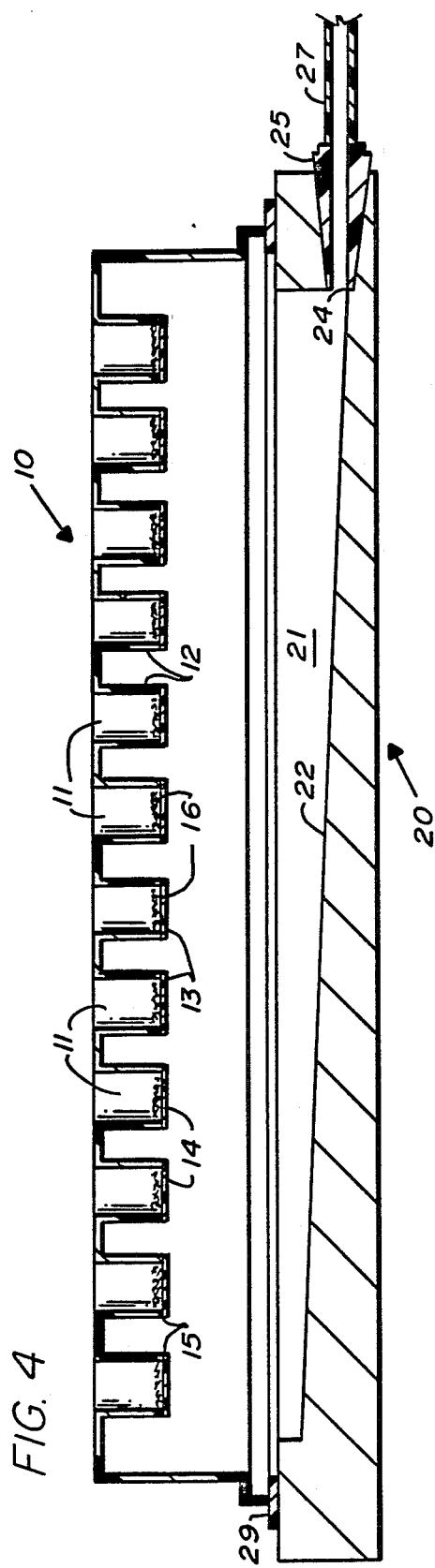
FIG. 2
FIG. 4

MANIFOLD VACUUM DEVICE FOR BIOCHEMICAL AND IMMUNOLOGICAL USES

REFERENCE TO RELATED APPLICATION

This application is a continuation-in-part of application Ser. No. 856,647, filed Apr. 25, 1986, now abandoned.

This invention relates to a novel manifold device such as a microtiter tray assembly and its combination with a vacuum device.

BACKGROUND OF THE INVENTION

Biochemical and immunological testing of cellular and particulate matter typically involves a series of discrete reactions to attain the desired end product. Between successive steps of the reaction series, the cellular or particulate matter typically needs to be washed thoroughly or transferred to a new reaction vessel, or both, prior to exposure to the reactants involved in the subsequent reaction step. Such precautions need to be followed in order to prevent the subsequent step or steps from being contaminated by unwanted fluid-phase components of earlier reactions. When reactions free from contamination are attained, the end product is either a fluid-phase or solid-phase entity which can be legitimately and reliably detected and quantified by such means as visual inspection, fluorescence, spectrophotometry, and radiography.

The attainment of legitimate and reliable end products critically depends on how well the solid-phase components can be isolated from fluid-phase components during washing and transfer procedures. Over the years, various methodologies have been developed to facilitate the separation of solids from fluids. Older methodologies include centrifugation, gravity filtration, vacuum-assisted filtration, gravity separation, adsorption, and a variety of differential separation techniques based on molecular weights, conformation, etc. In the case of centrifugation, separation and adsorption techniques, the fluid-phase needs to be decanted or otherwise drawn off from the isolated solid phase before transfer or further washing steps can be accomplished. These techniques are all time consuming and subject to contamination whenever removal or transfer of components occurs.

Filtration has multiple advantages over the other techniques listed above. First, filtration is generally less time consuming, especially when filtration is assisted by applying a vacuum across the base of the filter. Second, the need to decant or draw off the fluid phase is avoided (as is this potential source of contamination) by the choice of filtering material. When properly chosen, the filter material forms a mesh with a large surface area to bind the solid-phase biological coreactant while allowing the fluid phase to pass through unimpeded. Third, the solid material can be multiply washed while being bound by the solid-phase support, thereby both facilitating the speed and ease of the wash steps as well as minimizing the problem of contamination. Fourth, concentration of the coreactant bound to the support material both increases the efficiency of transfer of this material to subsequent reaction vessels and enhances detection of the final solid-phase reaction product.

Recent advances in biochemical micromethods have focused on the advantages offered by filtration. Prior to incorporation of filtration techniques, biochemical reactions were carried out in test tubes or, when simultaneous testing of multiple small samples was desired, in commerically available manifolds consisting of an array of small tubes held together in a grid pattern. The lack of filtration capabilities in these earlier methodologies meant that these techniques were constrained by the limitations imposed by centrifugation, adsorption, and separation technologies, as described above. These limitations have been overcome within the last five years by incorporation of new filtration techniques into existing biochemical micromethodologies.

The earliest of these was described by Cole and Van Voorhis (U.S. Pat. No. 4,407,943; Oct. 4, 1983). In this device, antigens are immobilized on a membrane composed of interconnecting networks of pores to provide a large surface area for reactions to occur. This membrane was attached across the base of the reaction well, such that reaction fluids placed within the reaction well then flowed, due to hydrostatic pressure, through the tortuous course of the membrane, and then dripped off the underside of the membrane into a waste fluid collection chamber. Rate of flow through the membrane, and hence the time allowed for fluid components to interact with the bound antigen, was regulated by the diameter of the membrane pores and the volume of reaction fluid (hence the amount of hydrostatic pressure attained as a driving force) placed in the reaction well.

Although the invention of Cole and Van Voorhis represents a definite step forward in micromethodology, more recent approaches have recognized that increased sensitivity can be achieved if the reaction fluids are retained within the reaction well until drawn out of the well by vacuum filtration.

To date, three major approaches have been taken to merge vacuum filtration capabilities with biochemical micromethods. Although differing in design (see below for details), these three approaches all share one primary concept; that is, replacing the non-permeable bottom of the reaction vessel with a permeable material which overlies a low-resistance port through which fluid can pass upon application of vacuum.

By this single design change, two major advances were attained over prior methodologies. First, upon addition of the reagents, the biochemical or immunological reaction commenced and continued within the vessel until such time as the fluid components were evacuated from the vessel by vacuum applied across the permeable base of the reaction vessel. This meant that the same vessel was used for the reaction as well as for the separation of the solid phase from the fluid phase. Second, transfer of the reaction product to a new vessel for each reaction step was obviated, due to the efficiency in washing the vessel and reaction product afforded by this technique. In sum, then, this basic design change enhanced the speed, efficiency and specificity of biochemical and immunologic reactions.

Although this basic design change was common to all three currently available variations of vacuum-based biochemical micromethodologies, the three differed significantly in their approaches, and each had its own constellation of strengths and weaknesses. The first vacuum-based biochemical micromethod was introduced by Cleveland (U.S. Pat. No. 4,427,415; Jan. 24, 1984). In the commerically available version of his device, Cleveland modified a standard 96-well (8×12 matrix; volume of each flat-bottomed well=approx 350 μl) microtiter tray by piercing the center of each well bottom to form a small (approximately 22 gauge) drain hole. The size of this drain hole was such that the surface tension of the fluids within the well prevented flow through the hole until vacuum was applied across the base of the microtiter tray. Positioned within each well, directly above the drain hole and covering the entire well bottom, was a circular disk of Whatman 934/AH glass microfiber filter material. The filter material served to trap the solid-phase reaction product when the fluid phase was evacuated from the well interior through the filter under vacuum.

However, multiple problems were inherent in this Cleveland technique. First, the drain hole was small. While this restriction was needed in order to attain the necessary surface tension to retain fluid within the well, this restriction in turn produced a very low bubble point. That is, the fluid being evacuated under vacuum through the drain hole bubbled and sprayed as it exited, especially when vacuum pressure was elevated or when the fluid had any inherent tendency to foam, as is true for most washing or blocking buffers (i.e., protein-based buffers such as albumens, gelatins, or milk). This low bubble point had the marked disadvantage of contaminating the reactions occurring in neighboring wells, due to spread of reagents between wells.

Second, the Cleveland drain hole was small and was located only under the center of the filter. Since effective washing of the trapped solid-phase component and effective removal of unreacted substrate are both critical to the specificity of the final reaction product attained, the device gave rise to problems. It resulted in uneven washing, since the vacuum was highest directly over the drain hole and was minimal at the lateral edges of the circular filter. This, in turn, led to a disparity in the effectiveness of the wash steps in the center, as against lateral, regions of the filter, as well as producing a tendency for reaction fluids to become trapped between the lateral aspects of the filter and the non-permeable well base (lateral to the drain hole).

Third, the die-cut Whatman glass microfiber filters used by Cleveland were compressed, due to the manufacturing technique employed. This compression created regions which did not allow fluids to pass, thereby resulting in uneven deposition of the solid-phase reaction products and regions of ineffectual washing.

These problems were overcome, in part, by structures such as those of Cleveland (U.S. Pat. No. 4,427,415; Jan. 24, 1984) and Fernwood and Burd (U.S. Pat. No. 4,493,815; Jan. 15, 1985). In each of these devices, a modified microtiter tray was used, such that the base of each of the ninety-six wells was removed, leaving the cylindrical wells completely open on both ends. The open-ended wells were then placed upon a single large sheet of filter material, which, in turn, rested across the bases of all wells. The filter material, in turn, rested upon a plate containing ninety-six drain holes which were aligned with the centers of the ninety-six wells above the filter material. This "plate-filter-plate sandwich" was then tightly clamped together, so that the lowest-resistance pathway for fluid placed in the wells was through the filter material and out through the drain holes in the base plate. By extending the length of the drain holes, cross-contamination due to the low bubble point was minimized. However, waste fluids which remained within the elongated exit port could contact the base of the filter material and contaminate the reaction occurring within the overlying well. These devices did not address the problem of uneven washing, which arose due to the uneven vacuum pressure applied across the lateral extent of the filter. Additionally, the required use of sheets of filter material restricted the choice of filters to materials such as nitrocellulose and bioaffinity membranes which have unidirectional pores, totally negating the use of glass microfiber or paper filter materials which draw fluids laterally between wells with remarkable tenacity. This capillary action of the microfibers and paper fibers cannot be overcome by any of the above-mentioned designs.

The last, and most recent, of the three major advances prior to the present invention is exemplified by Kiovsky and Hendrick (U.S. Pat. No. 4,526,690; July 2, 1985). Their manifold was again designed to overcome inadequacies inherent in the previous designs, yet their manifold was plagued by its own unique problems. The Kiovsky and Hendrick plate employed a ninety-six well microtiter plate where, as in the plate described in the previous paragraph, the entire bases were removed from all wells. Heat sealed to all of the bases of the ninety-six wells was a set of three sheets. The innermost sheet (that is, the one in direct contact with the wells) was a nitrocellulose material and the outer two sheets (that is, those further from the wells) were colandered Tyvek. The non-wettable, hydrophobic characteristics of Tyvek allowed fluid to be retained within the wells in the absence of applied vacuum, and the colandered processing of the Tyvek allowed fluid to be drawn through this material under vacuum. The nitrocellulose material provided a surface for collecting solid-phase reaction products and was thin enough to allow heat sealing to occur between the microtiter plate material and Tyvek.

The major advantage of this Kiovsky and Hendrick modification was that even vacuum pressure was applied across the entire filter surface, instead of maximally over a small drain hole as in previous methods. The purpose was to provide a more uniform wash of solid-phase materials and removal of fluid-phase reactants. A second advantage of this modification was that filter material was not die cut; so there were no compressed regions resulting in uneven concentration of solid-phase products. A third advantage was that, though a bubble point was definitely attainable during normal usage of this device, it was higher than in the first device described, since the surface area over which vacuum was applied was much greater.

Despite these advantages, this Kiovsky and Hendrick manifold suffered from several flaws. First, the user was restricted to using fragile, paper-thin filter material like nitrocellulose, since thicker filter materials (such as paper or glass microfibers) prevented the manifold-to-Tyvek heat sealing from occurring. This presented a problem since nitrocellulose is inappropriate for many filtering needs due to the small (0.5–5.0 micron) pore sizes which clog during many applications. Second, the filter material was a single sheet bound to all ninety-six wells, which meant that the filter, and the solid-phase reaction product trapped upon it, could not be easily removed upon completion of the reaction procedure for further testing of the reaction product or storage of the test results. Although the filter could be cut away from each well upon completion of the reaction for further testing or storage, the nitrocellulose material is extremely fragile and does not lend itself to this procedure, but rather cracks and tears unevenly. Further, removal of single filters disrupted the integrity of the Tyvek base, which in turn destroyed the vacuum seal required for filtering. Fourth, cross-contamination between wells was a serious problem with this manifold design. Not only was the bubble point reached under normal usage (resulting in spraying and bubbling of fluid-phase components as they exited the wells), but also the use of a continuous sheet of Tyvek across the entire matrix of 96 wells provided a surface which the bubbles and spray could cling to, thereby increasing the probability of cross-contamination between wells. This cross-contamination occurred despite the fact that the heat-seal design of this plate should have theoretically decreased the chance of cross-contamination, since the heat-seal which ringed the base of each well was hydrophobic and tended to keep the fluid being evacuated from each well inside the hydrophobic ring. However, if fluid did cross this ring (as occurred when the plate was jostled during the reaction procedure or when the contents of any of the ninety-six wells bubbled during the vacuuming steps), the hydrophobic nature was destroyed and there was no resistance to fluid movement across the Tyvek sheet.

Published International patent application WO No. 82/03690 of Björkman shows a hydrophobic membrane locked into—but not sealed to—a reaction vessel. The vessel has an inturned lower end, above which is a frustoconical chamber portion leading to an inverted frustoconical portion of the vessel which widens out to a tapered, nearly cylindrical, wall. These specially shaped vessels are separate from a rack having a series of recesses, although the publication states that the rack's recesses may serve as reaction vessels; if so, they provide the needed porous bottom (the hydrophobic membrane), presumably again by trapping the membrane in an enlarged recess above an inturned lower end of each recess for no sealing is shown or discussed. On top of the porous membrane a "depth filter", which may be hydrophilic, is applied to the upper surface of the porous bottom, and covers the pores thereof. According to the last claim therein, his hydrophilic filter is "pressed against the upper surface of the vessel bottom". The porous membranes actually used are said to have been "made of teflon and hydrophobized bottoms of hydrophilic polymeric material."

All the recesses in the Björkman racks lead down into narrow channels; the recesses and the reaction vessels are not wide open at their lower ends. Moreover, it would be nearly impossible to manufacture such racks by injection molding or any other inexpensive process. The Björkman device is necessarily an expensive device, impractical for use in great quantity.

OBJECTS OF THE INVENTION

An object of the present invention is to provide a solid-phase vacuum device for biochemical and immunoligical tests, by which a large number of samples may be tested simultaneously.

Another object of the invention is to provide a test device made up of a matrix of reaction wells in each of which several sequential test steps can be accomplished without removal of the solid-phase components from the reaction wells between test operations.

Another object of the invention is to provide a test method in which large numbers of test samples may be processed without delays between steps being caused by having to decant or otherwise remove fluids, having to transfer the solid-phase material to other test containers, or mechanical separation.

Another object of the invention is to provide a test method that will separate free reagents from bound reagents rapidly and simultaneously for all samples.

Another object of the invention is to provide a device with small reaction chambers in order that only small volumes, in the order of 25 to 100 microliters, of costly or rare reagents need be used.

Another object of the invention is to provide a single manifold plate for various test steps of different characters, such as solid-phase separation, incubation, and mixing of samples in the same container, in order to minimize handling of samples in such steps.

Another object of the invention is to provide a simple, inexpensive device which will replace cumbersome, complicated and costly laboratory equipment currently required to perform the tests described above, which involve numerous sequential test procedures.

Another object of the invention is to provide a technological advance over currently available, and above-described, manifold vacuum devices, thereby increasing the versatility, ease of use, and dependability of the device as well as decreasing or even obviating problems of cross-contamination between wells and contamination within single wells.

SUMMARY OF THE INVENTION

The present invention retains the primary design concept central to all of three manifold vacuum devices; that is, replacing the non-permeable bottom of the reaction vessels with a hydrophobic permeable material which overlies a low-resistance port through which fluid can pass upon application of vacuum. As in previous designs, the entire plate is placed over a second solid element which contains a vacuum chamber large enough to cover the entire lower surface of the manifold arrangement of test wells in the upper plate. A gasket is provided to seal the juncture between the upper and lower elements and a vacuum line connection is provided through the lower element in order to apply reduced pressure to the vacuum chamber, thereby drawing fluid out of the test wells.

The present invention includes a solid plate containing an array of small wells for containment of biochemical or immunological samples, similar to the microtiter plates currently commercially available. The features unique to the invention, however, are found at the lower end of each well of the manifold assembly.

First, each well, rather than being a closed receptacle or opening into a narrow channel, is completely open at its lower end. A hydrophobic sheet-like membrane is sealed by heat to the lower end or base of each well, allowing fluids to pass through it either under vacuum or, alternatively, by contact on its lower surface, into or over any sort of wicking material such as cloth, cotton, cellulose, paper, sponges, plastic, etc. This novel structure prevents or minimizes the bubble-point problems and the problems of uneven washing or vacuuming, thereby solving the problems inherent in prior manifold designs incorporating a small drain port in the lower end wall of each well.

As an example of the within-described design, a manifold made from polyvinyl chloride (PVC) is compatible with a single layer of spun-bonded polyester (such as Hollytex) since their relative melting points allow a very strong heat seal to be attained easily between these two materials. However, other manifold and permeable membrane material combinations can be used, as long as a seal is attainable between them either by heat, chemical, physical or other similar means, and the membrane material has both hydrophobic and vacuum-induced permeability properties.

Second, unlike the Bjorkman device, the hydrophobic material completely covers the base of each well but, critically, does not extend beyond the walls of each well. That is, unlike the Kiovsky and Hendrick manifold, there is no physical continuity between the bases of adjoining wells, thereby obviating the serious problem of cross-contamination inherent in that prior design.

Third, the hydrophobic membrane supports a solid-phase support that binds biological coreactants. However, unlike the Kiovsky and Hendrick and the Fernwood and Burd manifolds, the herein-described manifold is compatible with any of the solid-phase supports that bind biological coreactants including cellulose, nitrocellulose, bioaffinity membranes, paper, and glass microfibers.

Fourth, unlike previous such devices, the within-described manifold does not require the use of any fluid-permeable material other than the hydrophobic membrane, thereby making it compatible with a variety of other entities, including sephadex, latex, and plastic beads, microspheres, and whole cells.

Fifth, since the hydrophobic membrane and only the hydrophobic membrane is sealed to the base of the well walls, the solid-phase support material can be easily removed from the wells for transfer or further analysis of the bound biological coreactants or storage of the test results.

Sixth, unlike the manifolds of Kiovsky and Hendrick, Cleveland, and Fernwood and Burd, wherein sheets of filter material are employed, the user is not restricted to using the same solid-phase support for biological coreactants in every well, but rather can use any combination of fiber support medium, beads, microspheres, whole cells, etc., changing from well to well.

Seventh, since the hydrophobic material remains undamaged when the fiber support medium beads, microspheres, whole cells, etc. are removed (unlike the case of any previous manifold), the vacuum seal is not broken, and the manifold still functions normally following removal of the fiber support medium beads, or other biologic or man-made material.

Thus, the present invention represents an advance over all previous manifold devices. While it facilitates immunodiagnostic testing which was previously cumbersome, time-consuming, and difficult to perform, the present device can also be used in conjunction with immunoasssys employing enzyme-labeled antibodies, direct radioimmunoassays, indirect radioimmunoassays, competitive inhibition radioimmunoassays, immunoassays employing fluorescently labeled antibodies, or other binding agents (such as staphylococcus aureus protein A) or antigens.

BRIEF DESCRIPTION OF THE DRAWINGS

FIG. 1 is a top view of an assembled microtiter device embodying the principles of the invention.

FIG. 2 is an enlarged view in section taken along the line 2—2 in FIG. 1 through one well.

FIG. 3 is an enlarged view in horizontal section taken along the line 3—3 in FIG. 2.

FIG. 4 is a view in vertical section taken along the line 4—4 in FIG. 1.

DETAILED DESCRIPTION OF THE PREFERRED EMBODIMENT

Figure 5:
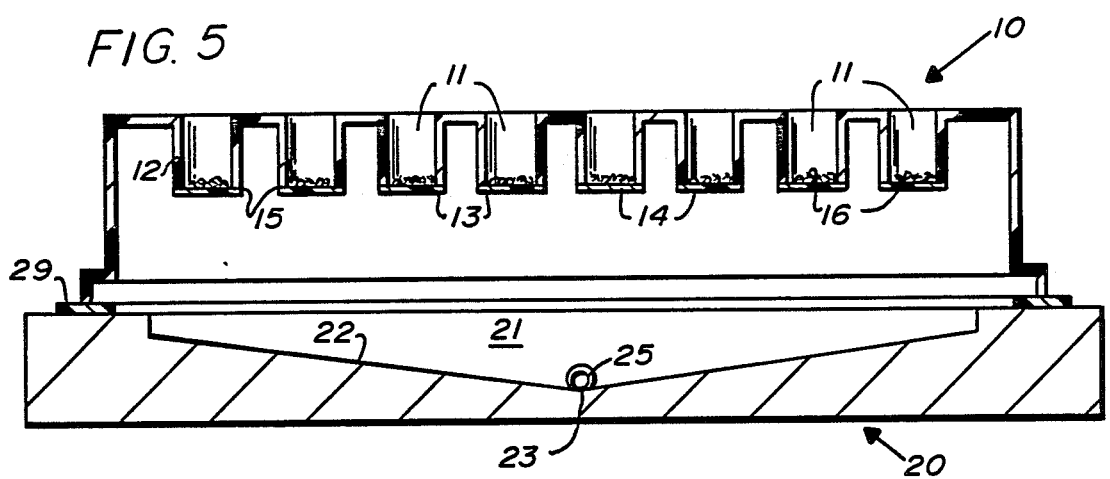
FIG. 5 is a view in vertical section taken along the line 5—5 in FIG. 1.

As shown in FIGS. 1, 4, and 5, a manifold plate 10 contains a grid array of wells 11 which serve to hold a reaction mixture. The manifold plate 10 may be any suitable material, e.g., metal, glass, or plastic, such as polyvinyl chloride, polypropylene, or polyestyrene. The wells 11 have vertical, preferably cylindrical or slightly conical, walls 12 that are impermeable to fluids. If plastic is used for the plate 10, it must be sufficiently rigid not to implode when vacuum is applied. This is a function of the structural design, as well as, of the material and thickness. Injection-molded polystyrene with walls 0.8 mm thick and form-molded polypropylene about 0.08 mm thick have been used.

As best seen in FIG. 2, each well 11 has an annular, planar base 13 at its lower end, to which is sealed a hydrophobic, fluid-permeable membrane 14 of material such as spun-bonded polyester. The membrane 14 closes the lower end of the well around the complete circumference of the lower edge or base 13 of the wall 12 with a heat or adhesive seal 15. Note that the membrane 14 covers the entire lower end of the well 11 but does not extend beyond it. It may therefore be a disk. This is also shown in FIGS. 4–9. The permeable membrane 14 thus serves as the bottom covering at the base 13 of each well 11. Since there is no physical continuity between the membrane 14 of adjoining wells 11, the serious problem of cross-contamination is solved.

A preferred underlying permeable membrane material is Hollytex, which is a spun bonded polyester in a sheet of continuous-filament polyester fibers that have been compacted by a process involving simultaneous application of heat, pressure, and tension. Style #3257 has a nominal basis weight of 1.0 oz/yd$^2$ and a thickness of 0.0025 inch. Its air permeability is 300 CFM/Ft$^2$, and its tensile strength is 9 pounds in the machine direction and 7 pounds in the cross direction. The elongation of this material is 40% in the machine direction and 50% in the cross direction.

As FIGS. 2 through 9 show, a solid-phase support 16 for biological coreactants lies within each well 11 above the base 13. The wells 11 and their membranes 14 are able to support any solid-phase support material, including cellulose, nitrocellulose, bioaffinity membranes, paper, and glass microfibers. Moreover, since no support material is required above the hydrophobic membrane 14, the wells 11 and their base 13 can hold and support a variety of other entities, including sephadex, latex, and plastic beads, microspheres, and whole cells.

To use the manifold 10 as a vacuum device, the entire manifold 10 may be placed over a solid receptacle 20, (FIGS. 4 and 5), so that the array of wells 11 overlies a single vacuum chamber 21 with a sloping imperforate floor 22. Preferably, the floor 22 slopes down toward its centerline 23 and toward one end. The lowest point 24 of the floor 22 lies at the inner end of a vacuum nipple 25. The nipple 25 is connected to a vacuum source 26 via tubing 27 (FIG. 1), in order that fluids drawn through the membranes 14 during the application of vacuum, collect at the vacuum nipple 25 and are withdrawn and sent through a disposal line 28. The juncture between the manifold plate 10 and the receptacle 20 is formed by a gasket 29 which provides a seal between the manifold 10 and the receptacle 20 when vacuum is applied.

Figure 6:
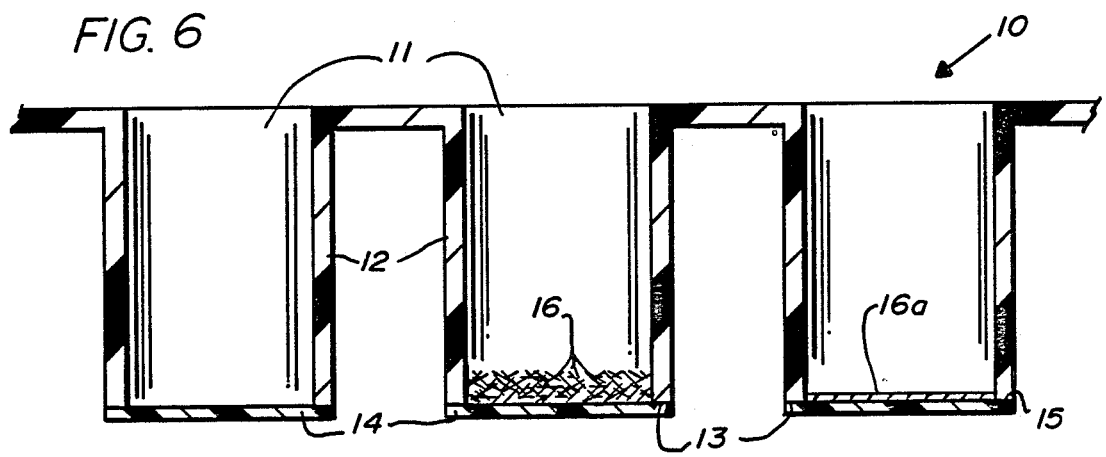
FIG. 6 is a partial vertical cross-sectional view across the manifold plate on an enlarged scale, from left to right, showing three wells closed at their lower ends by the heat-sealed membrane, one well being without an overlying support for bonding biological coreactants, one well with such an overlying support of glass microfibers, and one well with such an overlying support of nitrocellulose.

FIG. 6 illustrates three wels 11 with different treatments thereof. At the left the well 11 is shown without any solid-phase support material, other than the membrane 14. In the center well 11 there is an overlying solid-phase support 16 of glass microfibers, while in the right well 11 there is an overlying solid-phase support 16a of nitrocellulose. Any of a variety of suitable solid-phase support materials 16 or 16a can be introduced into the wells 11 above the membrane 14. In this invention the user is not restricted to using the same material in every well, but rather can use any combination of filter materials, beads, microspheres, whole cells, etc., changing from well to well.

Figure 7:
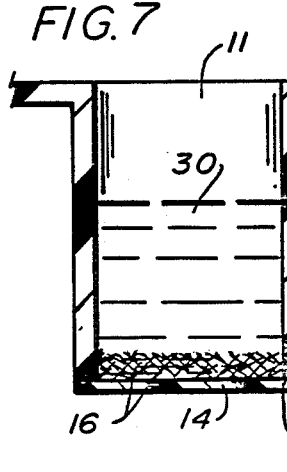
FIG. 7 is a similar partial cross-sectional view of the manifold plate, illustrating retention of the reaction fluid within one well.

FIG. 7 illustrates a reaction occurring within a well 11, in a liquid mixture with the biological coreactant being bound to the mesh-like solid-phase support material.

Figure 8:
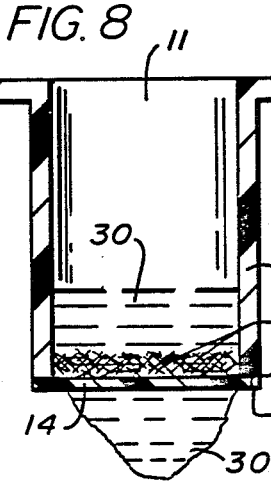
FIG. 8 is a partial cross-section of the manifold plate illustrating flow of the fluid phase through the solid-phase support and the membrane of one well upon application of vacuum across the lower ends of the wells.

FIG. 8 illustrates the well 11 of FIG. 7 after completion of the reaction, when vacuum is being applied to draw the reaction fluid 30 out of the well 11 through the membrane 14, while retaining the solid-phase reaction products bound to the solid-phase support 16 within the well 11.

Figure 9:
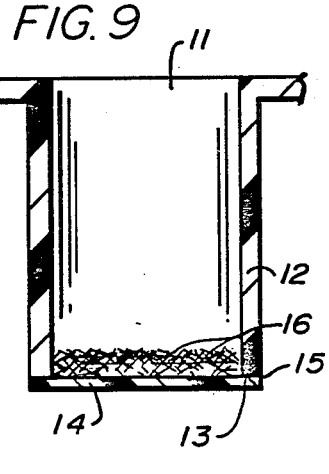
FIG. 9 is a partial cross-section of the manifold plate illustrating a voided well upon completion of the vacuum phase.

FIG. 9 illustrates the same well upon completion of the process, wherein the well 11 is void of fluid, and the solid biological reactants remain bound to the solid-phase support medium 16. Since only the hydrophobic membrane 14 is sealed to the well walls 12, the solid-phase support material 16 can be easily removed from the wells 11 for further analysis of the bound coreactant or for storage of the test results. Since the hydrophobic-material membrane 14 remains undamaged when the solid-phase support material 16 or beads, microspheres, whole cells, etc. are removed, the vacuum seal of the membrane 14 to the base 13 of the walls 12 is not broken, and the manifold 10 still functions normally following removal of the solid-phase support 16, beads, or other biologic or man-made material.

The present device can be used in conjunction with immunoassays employing enzyme-labeled antibodies, direct radioimmunoassays, indirect radioimmunoassays, competitive inhibition radioimmunoassays, immunoassays employing fluorescently labeled antibodies, or other binding agents, such as staphylococcus aureus protein a or antigens.

The device and methodology presented herein were originally developed to facilitate immunodiagnostic tests in the blood bank, which are tedious to perform. Such tests involve the detection and identification of unexpected antibodies in a blood recipient which would preclude transfusion of blood containing red cell antigens reacting against these antibodies. Current methods involve the repeated treatment and washing of test cells prior to reaction with the antibodies, whereas, such procedures are not necessary with the invention described herein. Such methodology replaces previous cell agglutination detection with a standardized color end product, thus allowing instrumental quantitation of the endpoint. The cell agglutination endpoint for all practical purposes is a subjective visual system. The present system has also been used for large scale reverse grouping of blood prior to transfusion. That is, to verify the blood group of a donor, the red cells are tested with antibodies directed against the major ABO groups. Patients having a blood group of A, for instance, will have antibody against group B. Conversely, group B subjects will have anti-A antibodies. Therefore, testing the antibodies can confirm the accurate grouping of the red blood cells. Such testing is performed in test tubes and involves cumbersome handling of many tubes. In contrast, the present invention greatly streamlines the production of test results, since many tests can be made simultaneously in the same device. Since this invention can test for virus antibodies such as HIV (associated with Acquired Immunodeficiency Disease Syndrome) or hepatitis, such viral testing can be combined with the batch testing of red cell antibodies as described above.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A microtiter tray for use with a vacuum chamber therebelow, comprising:

a manifold plate formed to define a series of substantially cylindrical, wells with fluid-impermeable walls having inner and outer surfaces, each said wall having a planar, annular base at its lower end surrounding a circular bottom opening of said well the full diameter across said wall's upper surfaces, a series of separate hydrophobic, liquid-permeable membranes means, each secured to and sealed to the lower surface of a said base of one said well, for closing the lower end of said well along a flat plane and for enabling said wells to contain a reagent sample to be tested, without leakage so long as no significant pressure differential exists between the upper and lower surfaces of said membrane means and said membrane means' lower surface is retained free from contact with an absorbent material, said membrane means affording passage of said sample under significant pressure differential and when in contact with absorbent material, each said membrane means having an outer periphery separated from the outer periphery of all adjacent wells, so that fluid cannot migrate from one to another, and having a solid-phase means for supporting a biological coreactant for bonding thereto a reaction product resulting from said reagent, contained in said well above and itself supported by said membrane means.

2. The microtiter tray of claim 1 wherein the outer periphery of each said membrane means extends out no further than the outer surface of the walls of its well.

3. The microtiter tray of claim 1 wherein said membrane means is a spun-bonded polyester in a sheet of compacted continuous-filament polyester fibers.

4. A inexpensive, disposable microtiter tray for use with a vacuum chamber therebelow, comprising:
   a manifold plate formed of plastic to define a series of fluid-impermeable substantially cylindrical wells fully open at their lower ends, each well having a cylindrical well with a planar, annular base at its lower end, and
   a series of separate hydrophobic, liquid-permeable membranes, each permanently secured to and sealed to the lower surface of a said planar base of one said well to close said well for temporary containment of a liquid comprising a reagent sample nonreactive with said plastic and said membrane during incubation and the like, while being sufficiently spaced from the membrane of all adjacent well to prevent fluid migration thereto, and
   each said membrane providing passage through it of said liquid without binding a reagent from said liquid, when subjected to significant pressure differential above and below said membrane, and a solid-phase porous fiber means within atleast some of said wells, and freely withdrawable therefrom, each above and detached from a said membrane, for supporting a biological coreactant for bonding to a reaction product of said reagent with said correaction.

5. The microtiter tray of claim 4 in which each said membrane has an outer periphery substantially coincident with that of its well.

6. The microtiter tray of claim 4 wherein said membrane is a spun-bonded polyester in a sheet of compacted continuous-filament polyester fibers.

7. A microtiter tray-vacuum chamber combination comprising:
   a manifold plate formed to define a series of fluid-impermeable wells having substantially cylindrical walls and fully open at their lower ends, each wall having a planar, annular base portion at its lower end, and
   a series of separate hydrophobic, liquid-permeable membrane means each secured to and sealed to the lower surface of a said base of one said well, for closing the lower end of said well along a flat plane and for enabling said wells to contain a reagent sample to be tested without leakage so long and only so long as no significant pressure differential exists between the upper and lower surfaces of said membrane and said membrane's lower surface is retained free from contact with an absorbent material, each said membrane means having an outer periphery separated from the outer periphery of all adjacent wells, so that fluid cannot migrate from one to another,
   a lower receptacle beneath said manifold plate providing a vacuum chamber with an imperforate floor underlying said plate, said lower receptacle providing an outlet from said vacuum chamber, and
   a gasket sealing said plate to said lower receptacle and enclosing the vacuum chamber.

8. The combination of claim 7, wherein said lower receptacle provides a floor for said vacuum chamber that slopes toward said outlet.

9. The combination of claim 7 having solid-phase porous, fiber means within, and freely withdrawable from, at least some of said wells, each above and detached from a said membrane, for supporting a biological coreactant for bonding to a reaction product of said reagent with said coreaction.

10. The combination of claim 7 wherein said membrane is a spun-bonded polyester in a sheet of compacted continuous-filament polyester fibers.

11. A laboratory assembly, comprising:
    a manifold plate formed of plastic to define a series of small volume, fluid-impermeable, smooth-bore wells, each well having a capacity of about 25-100 microliters and being fully opened at its lower end and providing a planar, annular base at its lower end,
    a series of separate hydrophobic, liquid-permeable membranes, each permanently secured to and sealed to the lower surface of a said planar base of one said well to close said well for temporary containment of a liquid comprising reagent samples nonreactive with said plastic and said membrane during incubation and the like, while being sufficiently spaced from the membranes of all adjacent wells to prevent liquid migration thereto,
    each said membrane providing passage through it of said liquid without binding a reagent from said liquid, when subjected to significant pressure differential above and below said membrane, and
    solid-phase support means for bonding biological coreactants, supported loosely in each said well by a said membrane for binding a selected reagent from a said liquid inserted in its said well,
    a lower receptacle beneath said manifold plate providing a vacuum chamber underlying said plate, said receptacle providing an outer from said vacuum chamber, said receptacle providing an imperforate floor for said vacuum chamber,
    a gasket sealing said plate to said receptacle and enclosing the vacuum chamber,
    a source of vacuum suction of sufficient strength to draw the liquid of said reagent samples through the fluid-permeable membranes leaving a reactant bonded to said coreactants on said solid-phase support means in said wells, and
    connecting means leading from said vacuum chamber to said vacuum source.

12. The device of claim 11 in which said floor slopes toward said outlet.

* * * * *